Figure 1:
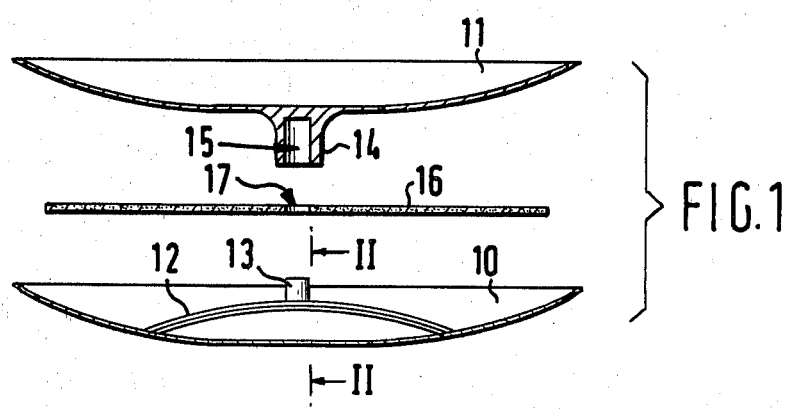

United States Patent [19]

Varndell

[11] 4,423,824

[45] Jan. 3, 1984

[54] CLOSURE DEVICE

[75] Inventor: John A. Varndell, Bagshot, England

[73] Assignee: Shell Internationale Research Maatschappij B.V., The Hague, Netherlands

[21] Appl. No.: 362,606

[22] Filed: Mar. 29, 1982

[30] Foreign Application Priority Data

Apr. 7, 1981 [GB] United Kingdom ................ 8110878

[51] Int. Cl.³ ...................... B65D 41/52; B65D 51/00
[52] U.S. Cl. ................................... 220/281; 215/256; 215/301; 4/293; 239/60
[58] Field of Search ............... 220/281; 215/301, 256; 239/60; 4/293, 295

[56] References Cited

U.S. PATENT DOCUMENTS

| 1,081,434 | 12/1913 | Cote | 4/293 |
|---|---|---|---|
| 2,024,227 | 12/1935 | Jones | |
| 2,362,250 | 11/1944 | Durst | 4/293 |
| 2,968,047 | 1/1961 | Stilborn | 4/295 |
| 3,136,415 | 6/1964 | Sandstrom | 206/403 |
| 3,484,016 | 12/1969 | Turner | 220/281 |
| 3,559,843 | 2/1971 | Kern | 220/281 |
| 3,876,102 | 4/1975 | Wharton | 215/358 |
| 3,934,745 | 1/1976 | Lovell | 220/281 X |
| 4,149,138 | 4/1979 | Pevzner et al. | 337/372 |
| 4,301,095 | 11/1981 | Mettler et al. | 239/60 X |

FOREIGN PATENT DOCUMENTS

| 2233383 | 1/1974 | Fed. Rep. of Germany . |
|---|---|---|
| 1253750 | 1/1961 | France . |
| 239460 | 9/1925 | United Kingdom . |
| 394613 | 6/1933 | United Kingdom . |
| 627747 | 8/1949 | United Kingdom . |
| 659994 | 10/1951 | United Kingdom . |
| 1358773 | 7/1974 | United Kingdom . |
| 1546526 | 5/1979 | United Kingdom . |

Primary Examiner—Donald F. Norton
Attorney, Agent, or Firm—William R. Hinds

[57] ABSTRACT

A closure device, which may serve as a bottle closure or as a sink plug, or may constitute a container such as for an air-freshener material, comprises a base and a lid, formed by a resiliently deformable disc, centrally resiliently mounted on a bridge spanning the base and capable of flexing reversibly between two stable dished conditions, respectively an externally convex closed form and an externally concave open form.

11 Claims, 7 Drawing Figures

U.S. Patent  Jan. 3, 1984  Sheet 1 of 2  4,423,824

CLOSURE DEVICE

The present invention is concerned with a closure device which is suitable for the quick opening or closing of an aperture. A variety of apertures may be so opened and closed. For example, the aperture can be one for gaining access to the interior of a container to enable the contents thereof, which may be a solid or fluid, to be removed or, in the case of vaporisable or vapour-emitting contents, to escape. As other examples, the aperture could be the gap between electrical contacts, in which case the closure device functions as a switch; or the aperture can be one between gripping surfaces. A particularly useful closure device provided by the invention is one which is embodied in or forms a container and operation of the device alternately opens and closes the container.

According to the invention, a closure device comprises a base and a lid, the lid being a resiliently deformable disc centrally resiliently mounted on the base and capable of flexing reversibly between and maintaining two stable dished conditions, respectively an externally convex closed form, in which the rim of the disc bears on or surrounds the base, and an externally concave open form, in which the rim of the disc is spaced away from the base.

Further features of the invention, which may be used individually or in combination, are that the resilient mounting of the lid is a resilient bridge spanning the central area of the base; the base and lid together form a container which may be charged with an annulus of solid material for exposure to the atmosphere when the lid is open; the base is formed as an insert for an aperture to be closed or opened by reversal of the form of the lid; the base is a sleeve for insertion in an aperture and the rim of the lid projects radially beyond the bore of the sleeve so as to close by bearing on the periphery of the sleeve or on a surround of an aperture in which the sleeve is inserted and may positively engage.

A closure device for the mouth of a container may have the lid initially sealed to the base, as by a tear-off strip, until first opening.

The lid disc is conveniently and preferably circular, this being the best shape for flexing reversibly between the two stable dished conditions, but it may be of oval or other flexibly reversible disc shape.

In a preferred embodiment, the closure device comprises a base and a circular, resilient dished lid, which lid in the closed condition of the device bears by its rim on the base or on the rim of an aperture in which the base is located and which lid is connected at its centre to a resilient element in the form of a bridge or spider upstanding from the base. The lid has a degree of resilience such that application of pressure on the lid at its centre can cause the lid to reverse its form from externally convex to externally concave, such reversal creating an opening between the lid and the base which, if the base is located in an existing aperture, opens that aperture. Normally the mechanical characteristics of the lid will be such that reversal of its form can be effected by the application of pressure to the periphery thereof when it is desired to re-close the lid against the rim of the base or the surrounding rim of an aperture.

The closure device of the present invention can be embodied in a wide variety of apertured equipment in which its ability to provide a snap opening and closing of an aperture can be utilised. The degree of resilience of the circular or generally circular disc lid, which resilience stems from the shape and mechanical characteristics of the disc, the physical properties of the material from which it is made and the fact that the base has a resilient element to which the disc is attached, is such that a snap reversal of the form of the device is achieved when appropriate pressure is applied to its centre or periphery. By snap reversal is meant that the disc does not dwell in intermediate positions but assumes the one or other of its stable positions when caused to move. Such movements can result in a gripping action being exerted on an article located in the aperture when the closure device is operated to cause the disc to move to the externally convex closed position. This potential gripping ability opens the possibility of a variety of applications.

However, at present the particularly preferred applications of the closure device of this invention are those in which it is embodied in and forms an integral part of a container or forms means for closing an existing aperture in or against which the device is located, and simply for ease of further description and exemplification those aspects of the invention will be emphasised hereinafter.

For example, in one form, the closure device comprises a base and lid, which together form a container for holding a solid material such as a vaporisable material as used in air fresheners. Operation to create an annular opening provides access to the solid. The solid is conveniently in the form of a disc with a central hole. The base of the closure device has a resilient bridge to which the lid is attached, and the connection between the lid and the bridge of the closure device is a boss upstanding from the bridge and extending into or through the hole for engagement in a socket on the underside of the lid. In one particular form, the bridge is a curved narrow strip of flexible plastics material which at its ends is bonded to, or moulded integrally with, the base, which itself may be upwardly concave, the bridge having at its mid-point a boss to pass through the hole in the contained product and fit as a spigot in a socket at the centre of the lid.

In another form, the base and lid are so constructed that the device forms a plug for an existing aperture such as a bath, sink or like outlet, the base in this case being sleeve-like or having a sleeved portion to enter and be retained in the aperture and the lid being arranged in the closed position to seal around the aperture. In a modification of this form the bridge may constitute the major part of the base, lugs being provided to extend into the aperture to frictionally engage fixed parts of the structure in which the aperture is provided to retain the device in position.

In yet another form, the device is designed to close the filling or discharge aperture of a container, for example, the neck of a bottle, jar or a like container, the base in this case being sleeve-like and insertable in the aperture, for example in the neck of a bottle, and the lid having at its rim a tear-off strip whereby the aperture can be sealed initially. After removal of the tear-off strip the aperture can be opened and closed as desired by reversing the dished shape of the lid.

Figure 2:
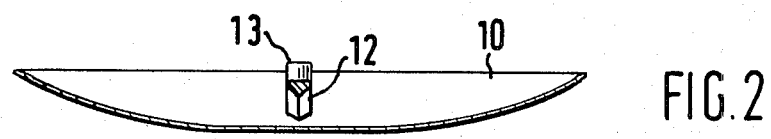
Figure 3:
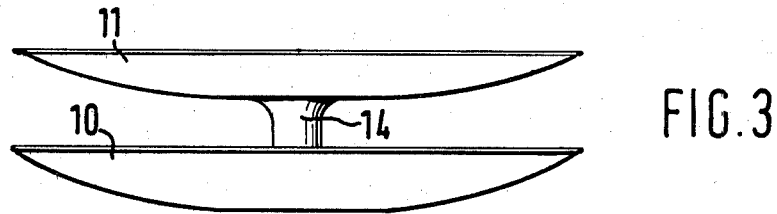
Figure 4:
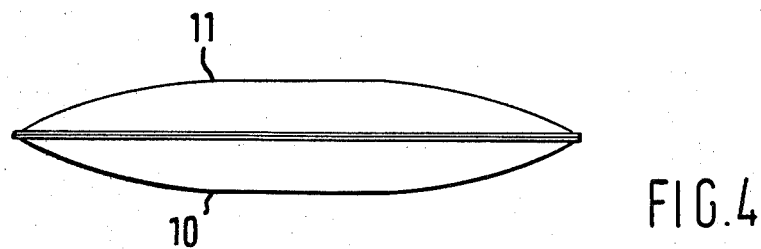
Figure 5:
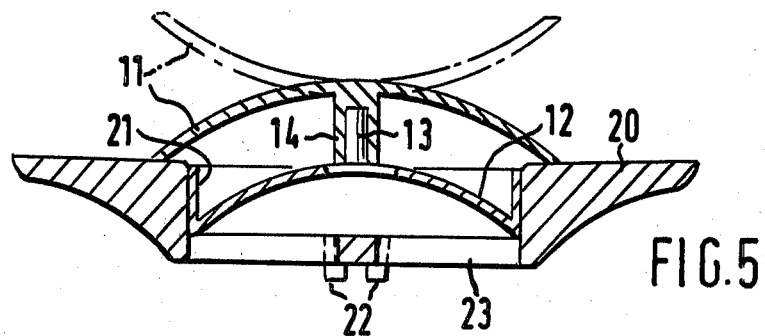
Figure 6:
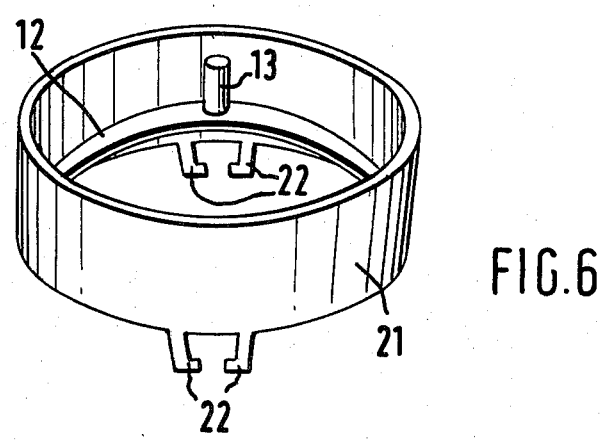
Figure 7:
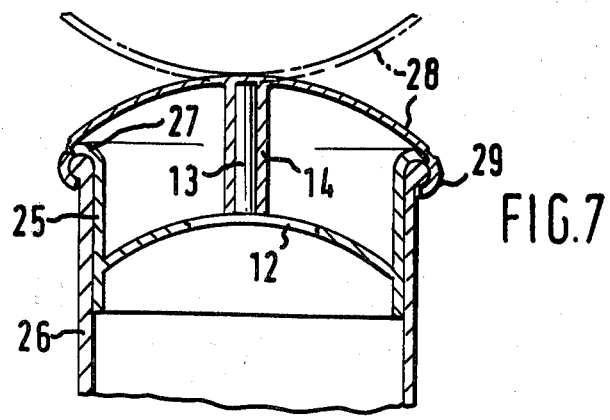

Some forms of this invention are illustrated in the accompanying drawings, in which:

FIG. 1 is an exploded view showing in axial section the components forming a container such as an air freshener container, FIG. 2 is a cross section of the base, on the line II—II of FIG. 1, FIG. 3 is a side elevation showing the container open, FIG. 4 is a side elevation showing the container closed, FIG. 5 shows in axial section a device forming a sink or like plug, FIG. 6 shows the base of the device of FIG. 5 in perspective, and FIG. 7 shows in axial section a device forming a bottle or like closure.

Referring now to FIGS. 1 to 4, the device shown is a container and comprises a base 10 and lid 11, both moulded from plastics material, which is advantageously polypropylene, polyethylene or a plastics material of similar mechanical properties. Both the base 10 and lid 11 are of circular form and of the same diameter so that in the closed, opposed dish, condition their rims are in contact.

The base 10 has moulded, bonded or otherwise made in one with it a bridge shown as an upwardly curved, narrow strip 12 of plastics material. The strip is of triangular cross-section and has at its centre an upwardly projecting boss 13. Instead of a single strip, the bridge could be a three-legged or other spider.

The lid 11 is resiliently flexible so that it can be made to snap reversibly between externally concave and convex stable forms. The lid 11 has at its centre a boss 14 with a socket 15 to receive as a spigot the boss 13.

The container charge in this example is of air-freshener material and is shown as a thin circular disc 16 with a hole 17 at its centre to engage over the boss 13.

To open the container from the closed condition (FIG. 4), pressure is applied to the centre area of the lid 11 so depressing the centre of the bridge. Since the rims of the base 10 and lid 11 are in contact, the upward reaction pressure at the rim of the lid causes the rim to be deflected upwards relatively to its centre and the lid reverses its form from externally convex to externally concave (FIGS. 1 to 3).

In FIGS. 5 and 6, the device is a plug for a bath or sink outlet 20 and differs from the construction of FIGS. 1 to 4 in that the base is a sleeve 21 which fits in the outlet 20 and has integral hooks 22 to provide a means of retention, positively engaging with an outlet grid 23. The remaining parts are substantially the same as in FIGS. 1 to 4, but it will be noticed that the lid 11 bears by its rim on the surround of the outlet 20, radially beyond the base 21.

In FIG. 7, the device is a closure cap for a bottle and the base in this case comprises a sleeve 25 which fits in the bottle neck 26 and has a flange 27 at its upper edge to overlie the rim of the bottle neck. The lid 28 is shown as having a tear-off strip 29 which is removed when first opening the bottle; thereafter the bottle is opened and closed by reversing the dished shape of the lid 28.

I claim:

1. A closure device comprising a base and a lid, the lid being a resiliently deformable disc generally centrally resiliently mounted on the base and capable of flexing reversibly between and maintaining two stable dished conditions, respectively an externally convex closed form, in which the rim area of the disc bears on a member selected from the group consisting of said base or a member about said base, and an externally concave open form, in which the rim of the disc is spaced away from the base; said resilient mounting of the lid being by resilient bridge means spanning at least part of said base.

2. A closure device as claimed in claim 1, wherein the resilient mounting of the lid is a resilient bridge comprising at least one resilient member spanning the central area of the base.

3. A closure device as claimed in claim 1 or 2, wherein the base and lid together form a container.

4. A closure device as claimed in claim 3, wherein the container is charged with an annulus of solid material for exposure to the atmosphere when the lid is open.

5. A closure device as claimed in claim 1 or 2, wherein the base is formed as an insert for an aperture to be closed or opened by reversal of the form of the lid.

6. A closure device as claimed in claim 5, wherein the base is a sleeve for insertion in an aperture and the rim of the lid projects radially beyond the bore of the sleeve so as to close by bearing on a member selected from the group consisting of the periphery of the sleeve or a surround of an aperture in which the sleeve is inserted.

7. A closure device as claimed in claim 6, wherein the sleeve has retaining means for positive engagement with the body having an aperture in which the sleeve fits.

8. A closure device as claimed in claim 1 or 2 and formed as a closure for the mouth of a container, the rim of the lid being initially sealed to the base until first opening.

9. A closure device as claimed in claim 8, wherein the rim of the lid is initially sealed to the base by a tear-off strip.

10. A closure device as claimed in claim 1, wherein at least the lid is moulded from a flexible plastics material such as polypropylene or polyethylene.

11. A closure device as claimed in claim 1 wherein said resilient bridge means comprises at least one curved strip of flexible material fixed at its ends to said base, and coupled at a point between its ends to said lid.

* * * * *